United States Patent [19]

Hung

[11] Patent Number: 4,604,461

[45] Date of Patent: Aug. 5, 1986

[54] 5-SUBSTITUTED-9-DISUBSTITUTED AMINO-12-SUBSTITUTED CARBONYLBENZO[A]PHENOXAZINES

[75] Inventor: William M. Hung, Cincinnati, Ohio

[73] Assignee: The Hilton-Davis Chemical Co., Cincinnati, Ohio

[21] Appl. No.: 772,096

[22] Filed: Sep. 3, 1985

Related U.S. Application Data

[62] Division of Ser. No. 636,461, Jul. 31, 1984, Pat. No. 4,570,171.

[51] Int. Cl.[4] .......................................... C07D 265/28
[52] U.S. Cl. ...................................................... 544/99
[58] Field of Search ........................................... 544/99

[56] References Cited

U.S. PATENT DOCUMENTS

| | | | |
|---|---|---|---|
| 3,704,298 | 11/1972 | Zinnes et al. | 544/49 |
| 4,309,255 | 1/1982 | Gendler et al. | 204/2 |
| 4,496,584 | 1/1985 | Fujii et al. | 560/139 X |

OTHER PUBLICATIONS

Buehler et al., Survey of Organic Chemistry, Wiley–Interscience, New York (1970), p. 264.
Sloviter, Journal of the American Chemical Society 71, 3360–3362 (1949).
Crossley et al., Journal of the American Chemical Society 74, 573–586 (1952).
Sen et al., Journal of Organic Chemistry 26, 3861–3863 (1961).

*Primary Examiner*—Richard L. Raymond
*Attorney, Agent, or Firm*—Terrence E. Miesle; Thomas L. Johnson; Paul E. Dupont

[57] ABSTRACT

5-[N-(RCO)-N-R[1]-amino] or (RCOO)-9-(N-R[2]-N-R[3]-amino)-12-(RCO)benzo[a]phenoxazines useful as color formers, particularly in electrochromic recording systems, are prepared by the interaction of the corresponding 5-(N-R[1]-amino)-9-(N-R[2]-N-R[3]-amino)benzo[a]phenoxazinium halide or 9-(N-R[2]-N-R[3]-amino)benzo[a]phenoxazin-5-one with a reducing agent to obtain the corresponding leuco compound and subsequently interacting the leuco compound with at least two molecular proportions of an acylating agent.

8 Claims, No Drawings

5-SUBSTITUTED-9-DISUBSTITUTED AMINO-12-SUBSTITUTED CARBONYLBENZO[A]PHENOXAZINES

This application is a division of my copending application Ser. No. 636,461, filed July 31, 1984, and now U.S. Pat. No. 4,570,171.

BACKGROUND OF THE INVENTION (a) Field of the Invention

This invention relates to novel compounds classified in the field of organic chemistry as benzo[a]phenoxazines, useful as color-forming substances, particularly in the art of electrochromic recording; to electrochromic recording systems containing said compounds; and to processes for preparing said compounds.

(b) Information Disclosure Statement

Several classes of organic compounds of widely diverse structural types are known to be useful as colorless precursors for electrochromic recording. Among the more important classes, there may be named leuco-type dyestuffs such as: phthalides, for example, crystal violet lactone, Malachite green lactone; fluorans, for example, 3-diethylamino-5,7-dimethylfluoran; and indolinobenzospiropyrans, for example, 1,3,3-trimethyl-6'-chloro-8'-methoxyindolinobenzospiropyrans. Also utilized as colorless precursors for electrochromic recording, either alone or in admixture with the leuco compounds indicated above, are substances known as redox indicators. The redox indicator which becomes colored in situ in the electrochromic recording process also is generally a leuco compound. Among the types of compounds which are applicable as redox indicators are phenothiazines, for example, leuco methylene blue and benzoyl leuco methylene blue. Other specific indicators are Leucoethyl Nile Blue, Leucomethyl Capyrl Blue and Leucosafranine T. Typical of the many such electrochromic recording systems taught in the prior art as those described in U.S. Pat. Nos. 3,726,769, 3,871,972, 3,864,684, 4,017,366, 4,133,933, and Re. 29,427 which issued Apr. 10, 1973, Mar. 18, 1975, Feb. 4, 1975, Apr. 12, 1977, Jan. 9, 1979, and Oct. 4, 1977, respectively. The methods for electrochromic recording taught in the prior art have many variations. Basically, a sheet of paper is coated or treated on one or both sides with a coating formulation containing at least one colorless color-forming (leuco) compound. Electrical current is then selectively applied to the coated side of the paper by some means, for example, a stylus or a printing head to which an electrical potential can be applied. The application of the current causes an electrochromic reaction involving the leuco compound to produce a visible image corresponding to the design traced by the stylus or that of the printing head.

The following items to date appear to constitute the most relevant prior art with regard to the instant invention.

Sloviter in Journal of the American Chemical Society 71 3360-3362 (1949) describes the preparation and properties of a series of halogenated benzo[a]phenoxazines having the structural formula

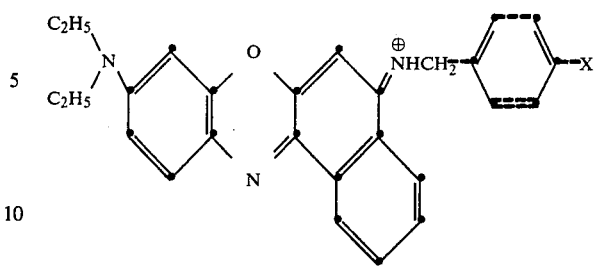

wherein X represents a hydrogen or a halogen. These compounds were prepared and studied for their ability to inhibit the growth of cancer cells.

Crossley et al. in Journal of the American Chemical Society 74 573-586 (1952) describe the preparation and properties of a series of 5-aralkylamino-9-dialkylaminobenzo[a]phenoxazines having the structural formula

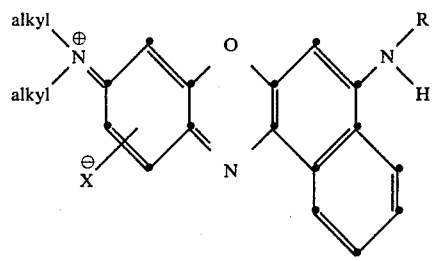

wherein R represents benzyl or ring substituted benzyl and X represents an anion of a salt. The compounds were prepared and studied as diagnostic and therapeutic agents in the study of cancer.

Sen and Shirley in Journal of Organic Chemistry 26 3861-3863 (1961) describe the preparation and properties of 12-acetylbenzo[a]phenoxazine and the corresponding chloroacetyl derivatives. These compounds were prepared to study chemotherapeutic agents against cancer cells.

U.S. Pat. No. 4,309,255, issued Jan. 5, 1982, discloses and claims a phenothiazine having the structural formula

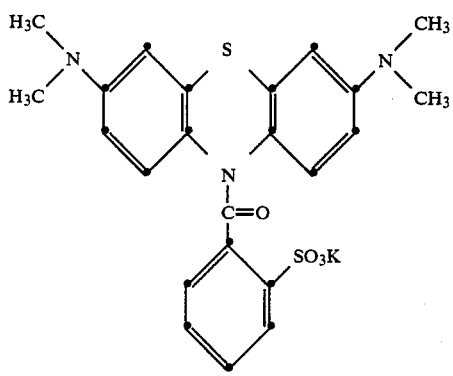

which is disclosed as being useful as a blue color former in electrochromic recording paper.

SUMMARY OF THE INVENTION

In its composition of matter aspect, the invention relates to certain 5-Q-9-(N-R$^2$-N-R$^3$-amino)-12-acylbenzo[a]phenoxazines useful as colorless precursors in electrochromic recording systems.

The present invention provides in its article of manufacture aspect, a substrate for use in electrochromic recording systems comprising a support sheet containing as a color-forming substance 5-Q-9-(N-R$^2$-N-R$^3$-amino)-12-acylbenzo[a]phenoxazines.

In its first process aspect, the invention relates to a process for producing 5-(N-R$^1$-N-acylamino)-9-(N-R$^2$-N-R$^3$-amino)-12-acylbenzo[a]phenoxazines which comprises interacting the corresponding 5-(N-R$^1$-amino)-9-(N-R$^2$-N-R$^3$-amino)benzo[a]phenoxazinium halide with a reducing agent to obtain the corresponding leuco compound and subsequently interacting the leuco compound with at least two molecular proportions of an acylating agent.

In its second process aspect, the invention relates to a process for producing 5-RCOO-9-(N-R$^2$-N-R$^3$-amino)-12-acylbenzo[a]phenoxazines which comprises interacting the corresponding 9-(N-R$^2$-N-R$^3$-amino)benzo[a]phenoxazin-5-one with a reducing agent to obtain the corresponding leuco compound and subsequently interacting the leuco compound with at least two molecular proportions of an acylating agent.

DETAILED DESCRIPTION INCLUSIVE OF THE PREFERRED EMBODIMENTS

More specifically, this invention in its composition of matter aspect resides in the novel 5-Q-9-(N-R$^2$-N-R$^3$-amino)-12-(COR)-benzo[a]phenoxazines having the structural formula

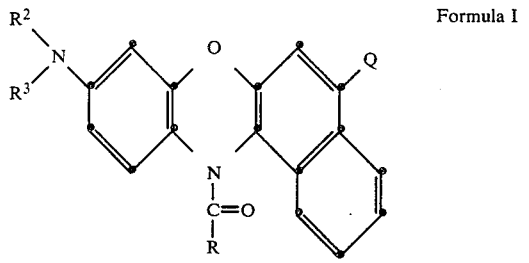

Formula I wherein Q represents [N-R$^1$-N-(RCO)amino] or (RCOO); R represents non-tertiary C$_1$ to C$_{12}$ alkyl, C$_4$ to C$_8$ cycloalkyl, non-tertiary C$_1$ to C$_{12}$ alkyl substituted by halogen, phenyl or phenyl substituted by one to three of non-tertiary C$_1$ to C$_4$ alkyl, non-tertiary C$_1$ to C$_4$ alkoxy, nitro, halo, phenyl, cyano or trihalomethyl; and R$^1$, R$^2$ and R$^3$ independently represent non-tertiary C$_1$ to C$_4$ alkyl, phenyl, phenyl substituted by one or two of halo, nitro, non-tertiary C$_1$ to C$_4$ alkyl or non-tertiary C$_1$ to C$_4$ alkoxy, benzyl or benzyl substituted in the benzene ring by one or two of halo, nitro, non-tertiary C$_1$ to C$_4$ alkyl or non-tertiary C$_1$ to C$_4$ alkoxy.

In a first particular embodiment in accordance with its composition of matter aspect, the invention sought to be patented resides in the novel 5-[N-R$^1$-N-(COR)-amino]-9-(N-R$^2$-N-R$^3$-amino-12-(COR)-benzo[a]-phenoxazines wherein Q represents [N-R$^1$-N-(COR)-amino] having the structural formula

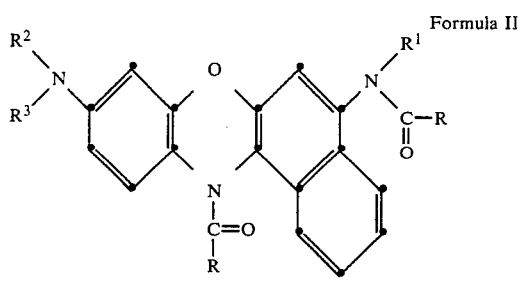

Formula II

Preferred compounds within the ambit of the first particular embodiment of the composition of matter aspect are the novel 5-[N-benzyl-N-(COR)-amino]-9-(N-R$^2$-N-R$^3$-mino)-12-(COR)-benzo[a]phenoxazines of Formula II wherein R$^1$ is benzyl.

In a second particular embodiment in accordance with its composition of matter aspect, the invention sought to be patented resides in the novel 5-(RCOO)-9-(N-R$^2$-N-R$^3$-amino)-12-(RCO)-benzo[a]phenoxazines wherein Q represents (RCOO) having the structural formula

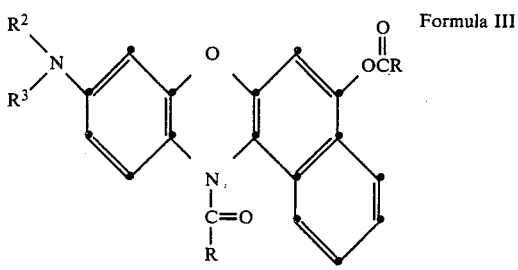

Formula III

In its first process aspect, the invention sought to be patented resides in the process for preparing a 5-[N-R$^1$-N-(COR)-amino]-9-(N-R$^2$-N-R$^3$-amino)-12-(COR)-benzo[a]phenoxazine according to Formula II which comprises in the first step, interacting 5-(N-R$^1$-amino)-9-(N-R$^2$-N-R$^3$-amino)benzo[a]phenoxazine-7-ium halide having the structural formula

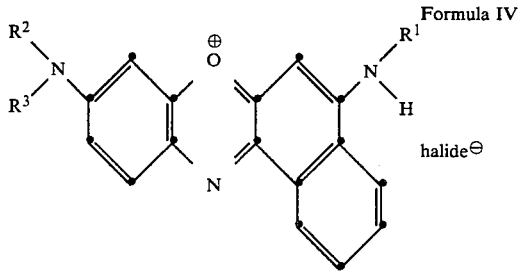

Formula IV with a reducing agent to obtain the corresponding leuco compound having the structural formula

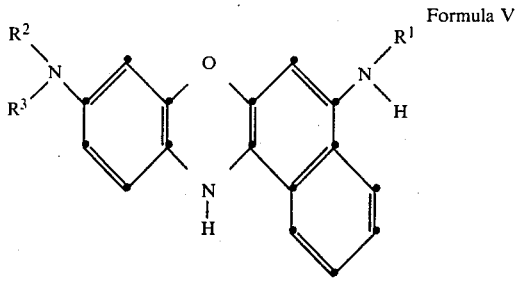

Formula V and in a second step, interacting the leuco compound with at least two molecular proportions of an acylating agent having the structural formula R—CO—Z        Formula VI in which Z represents halo or RCOO and R, $R^1$, $R^2$ and $R^3$ have the same respective meanings given in Formula II.

In its second process aspect, the invention sought to be patented resides in the process for preparing a 5-(RCOO)-9-(N-$R^2$-N-$R^3$-amino)-12-(COR)-benzo[a]phenoxazine according to Formula III which comprises in a first step, interacting a 9-(N-$R^2$-N-$R^3$-amino)benzo[a]phenoxazin-5-one having the structural formula

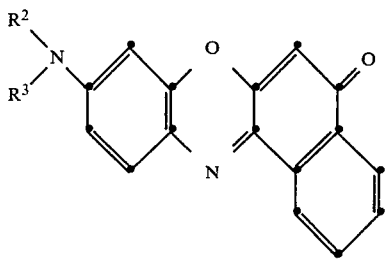

Formula VII with a reducing agent to obtain the corresponding leuco compound having the structural formula

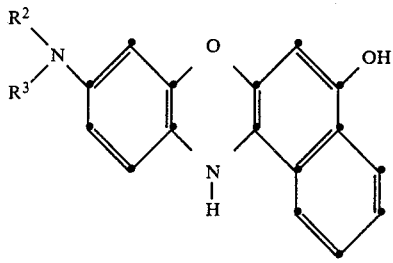

Formula VIII and in a second step, interacting the leuco compound with at least two molecular proportions of an acylating agent having the structural formula R—CO—Z        Formula VI in which Z represents halo or RCOO and R, $R^1$, $R^2$ and $R^3$ have the same respective meanings given in Formula III.

In its article of manufacture aspect, the invention sought to be patented resides in a substrate for use in electrochromic recording comprising a support sheet containing as a color-forming substance a 5-Q-9-(N-$R^2$-N-$R^3$-amino)-12-(COR)-benzo[a]phenoxazine having the structure of Formula I.

In a first particular embodiment in accordance with its article of manufacture aspect, the invention sought to be patented resides in the novel substrate for use in electrochromic recording comprising a support sheet containing as a color-forming substance a 5-[N-$R^1$-N-(COR)-amino]-9-(N-$R^2$-N-$R^3$-amino)-12-(COR)-benzo[a]phenoxazine having the structure of Formula II.

A preferred embodiment within the ambit of the first particular embodiment of the article of manufacture aspect is the substrate for use in electrochromic recording comprising a support sheet containing as a color-forming substance a compound of Formula II wherein $R^1$ is benzyl.

In a second particular embodiment in accordance with its article of manufacture aspect, the invention sought to be patented resides in the novel substrate for use in electrochromic recording comprising a support sheet containing as a color-forming substance a 5-(RCOO)-9-(N-$R^2$-N-$R^3$-amino)-12-(RCO)-benzo[a]phenoxazine having the structure of Formula III.

As used herein the terms "non-tertiary $C_1$ to $C_4$ alkyl" and "non-tertiary $C_1$ to $C_{12}$ alkyl" denote saturated monovalent straight or branched aliphatic hydrocarbon radicals including methyl, ethyl, propyl, isopropyl, butyl, isobutyl, amyl, 1-methylbutyl, 3-methylbutyl, hexyl, isohexyl, heptyl, isoheptyl, octyl, isooctyl, 2-ethylhexyl, nonyl, 3-ethylheptyl, n-decyl, n-undecyl, n-dodecyl and the like.

The term "non-tertiary $C_1$ to $C_4$ alkoxy" includes saturated acyclic, straight or branched-chained groups such as methoxy, ethoxy, propoxy, isopropoxy, butoxy, sec-butoxy and isobutoxy.

As used herein the terms "halo" and "halogen" include chloro, fluoro, bromo and iodo. Chloro is the preferred halo substituent because of the relatively low cost and ease of preparation of the required chloro-substituted intermediates and because the other halogens offer no particular advantages over chloro. However, the other above-named halo substituents are also satisfactory.

As used herein the term "$C_4$ to $C_8$ cycloalkyl" denotes saturated monovalent cyclic aliphatic hydrocarbon radicals including cyclobutyl, cyclopentyl, cyclohexyl, cycloheptyl, cyclooctyl and the like.

The benzo[a]phenoxazinium halides of Formula IV which are used as starting materials for the compounds of Formula II are generally known compounds readily prepared by procedures well known in the art. References for the preparation of benzo[a]phenoxazinium halides are: British Pat. No. 10,619; French Pat. No. 189,359; German Pat. No. 60,922; Journal of the Chemical Society 91 p. 324 (1907); Beilstein Handbuch der Organischen Chemie; Journal of the American Chemical Society 74, pages 573–586 (1952); and Journal of the American Chemical Society 71, pages 3360–3362 (1949).

The benzo[a]phenoxazin-5-ones of Formula VII which are used as starting materials for the compounds of Formula III are generally known compounds readily prepared by procedures well known in the art. References for the preparation of benzo[a]phenoxazin-5-ones are: Helvetica Chimica Acta 9, pages 868 and 880; and Chemische Berichte 50, page 881.

The acylating agents of Formula VI may be either aliphatic acid anhydrides or the acid halides (Z=halo, preferably chloro) both of which constitute well known classes of compounds many of which are commercially-available or are readily obtained by conventional synthesis well known in the art. The following list exemplifies aliphatic acid anhydrides and acid halides useful in carrying out the processes of this invention. Acetic anhydride, chloroacetic anhydride, dichloroacetic anhydride, trifluoroacetic anhydride, propionic anhydride, butyric anhydride, isobutyric anhydride, valeric anhydride, hexanoic anhydride, hepanoic anhydride, acetyl bromide, acetyl chloride, acetyl fluoride, bromoacetyl bromide, bromoacetyl chloride, chloroacetyl chloride, methoxyacetyl chloride, propionyl chloride, 2-bromopropionyl chloride, 3-bromopropionyl chloride, 2-chloropropionyl chloride, 3-chloropropionyl chloride, butyryl chloride, 4-chlorobutyryl chloride, 2-ethylbutyryl chloride, isobutyryl chloride, valeryl chloride, 5-chlorovaleryl chloride, isovaleryl chloride, 4-methylvaleryl chloride, hexanoyl chloride, 6-bromohexanoyl chloride, heptanoyl chloride, octanoyl chloride, nonanoyl chloride, decanoyl chloride, 10-undecanoyl chloride, palmitoyl chloride, myristoyl chloride, lauroyl chloride, cyclopropyl carboxylic acid chloride, cyclobutane carboxylic acid chloride, cyclohexyl carboxylic acid chloride, m-anisoyl chloride, p-anisoyl chloride, benzoyl bromide, benzoyl chloride, benzoyl fluoride, 4-biphenylcarbonyl chloride, 2-bromobenzoyl chloride, 4-bromobenzoyl chloride, 4-butoxybenzoyl chloride, 4-butylbenzoyl chloride, 2-chlorobenzoyl chloride, 3-chlorobenzoyl chloride, 4-chlorobenzoyl chloride, 4-cyanobenzoyl chloride, 2,4-dichlorobenzoyl chloride, 2,6-dichlorobenzoyl chloride, 3,4-dichlorobenzoyl chloride, 3,5-dimethoxybenzoyl chloride, 3,4-dimethoxybenzoyl chloride, 3,5-dinitrobenzoyl chloride, 2-fluorobenzoyl chloride, 3-fluorobenzoyl chloride, 4-fluorobenzoyl chloride, 3-nitrobenzoyl chloride, 4-nitrobenzoyl chloride, 2-methoxybenzoyl chloride, 3-methylbenzoyl chloride, 4-methylbenzoyl chloride, 2-iodobenzoyl chloride, 4-iodobenzoyl chloride and 4-trifluoromethylbenzoyl chloride.

The compounds of Formula I hereinabove are essentially colorless in the depicted form. When contacted with an electric current from an applied voltage stylus of the type ordinarily employed in electrochromic recording systems, the compounds of Formula I develop red-purple, purple, violet and blue-violet-colored images. These developed images are very insensitive to light, that is, once the color is developed, it remains unchanged when subjected to light exposure. The developed images also possess excellent xerographic reproducibility.

The compounds of this invention may be incorporated in any of the commercially-accepted systems known in the electrochromic recording art. Typical techniques for the application of the color formers to paper are well known and are described in numerous patents, for example, U.S. Pat. Nos. Re. 29,427; 3,726,769; 3,864,684; 3,871,972; 3,951,757; 4,017,366; and 4,133,933. The usual paper coatings consist of the color-forming component, an organic metal salt, a binder and some type of conductor, either an inorganic salt or a conductive polymer. This mixture is milled together optionally in the presence of a non-ionic surface active agent until the desired particle size is obtained and then the mixture is coated on paper and dried. Optionally, the color-forming substance can be milled in the presence of a binder and the remaining components milled also in the presence of a binder and the two mixtures combined together prior to coating on paper. Normally the surface of the coated paper is wet with a conductive solution containing an inorganic alkali metal or alkaline earth metal salt; for example, potassium chloride, calcium chloride, sodium chloride, sodium bromide, potassium bromide, potassium nitrate or sodium sulfate immediately prior to the printing with the applied voltage stylus. For a quick qualitative test, it has been determined that the color-forming component can be dissolved in a suitable volatile organic solvent, coated on paper and the coated paper dried to obtain a paper sheet coated with the color-forming component. This coated sheet can then be wet with a conductive salt solution and an image traced with an applied voltage stylus to develop the colored image.

The compounds of Formula I can be used alone as color-forming components in electrochromic recording paper or can be used in admixture with one or more other color-forming compounds from the classes consisting of phthalides, for example, Crystal Violet Lactone; fluorans, for example, 3-diethylamino-5,7-dimethylfluoran; redox indicators, for example, phenothiazines such as benzoyl leuco methylene blue and various other types of color-forming components currently employed in commercially-accepted electrochromic recording systems.

The best mode contemplated by the inventors of carrying out this invention will now be described so as to enable any person skilled in the art to which it pertains to make and use the same.

In accordance with one of the aforementioned process aspects of this invention, the compounds of Formula II are obtained by reacting approximately one molecular proportion of a leuco compound of Formula V with about two molecular proportions of an acylating agent of Formula VI. When using an anhydride as the acylating agent, the reaction is conveniently carried out in an excess of the acylating agent which is utilized as both the reaction medium and as the reactant. Optionally, a small amount of an organic base, for example, pyridine may be used as a catalyst. The reaction is conveniently carried out at a temperature in the range of 90° C. to reflux of the mixture for periods of approximately thirty minutes to approximately four hours. The compounds of Formula II thus obtained are isolated by pouring the reaction mixture into ice water and extracting the desired products into a suitable water immiscible organic liquid, for example, toluene. The organic liquid layer containing the product is subsequently washed with water to remove inorganic salts and water-soluble organics and then treated with decolorizing charcoal, if desired. The resulting organic liquid solution of the product is then concentrated by conventional means such as evaporation or distillation. Alternatively, the compounds of Formula II can be obtained also by reacting approximately one molecular proportion of a leuco compound of Formula V with about two molecular proportions of an acyl halide (Formula VI; Z=halo). A solution of the leuco compound dissolved in an organic liquid is heated to a temperature in the range of 60° to 80° C. and disodium phosphate and acyl halide, dissolved in the same organic liquid, is added. The reaction is conveniently carried out at the reflux temperature of the mixture for periods of approximately fifteen minutes to approximately nineteen hours. Water and additional disodium phosphate are added to the reaction mixture and the resulting mixture is heated at reflux temperature for a period of approximately thirty minutes to approximately one hour. The organic liquid solution containing the desired product is separated from the water layer, washed with water and concentrated by conventional means such as evaporation or distillation. The product of the concentration process is impure and further purification is desirable. The isolated product can be purified by conventional means such as recrystallization or reslurrying with a suitable organic liquid and then collected by filtration. Purification can also be effected by column chromatography. The material to be purified is dissolved in a suitable organic liquid and the solution is passed through a chromatography column which has been packed with a suitable substrate, for example, silica gel, cellulose or alumina. Numerous fractions are collected and analyzed to determine fraction(s) containing the desired product. The fraction(s) which contain the desired product are then combined (if more than one) and concentrated to obtain the product. The leuco compound of Formula V is conveniently prepared by reducing the corresponding benzo[a]phenoxazinium halide of Formula IV with a reducing agent, for example, an alkali hydrosulfite. The reaction in which the leuco compound is prepared is conveniently carried out in a mixture of water and a suitable water immiscible organic liquid, for example, toluene or xylene in an inert atmosphere, for example, nitrogen. The reaction is carried out in the presence of an alkaline substance, for example, sodium carbonate or disodium phosphate using, as the reducing agent, an alkali hydrosulfite, for example, sodium hydrosulfite. The reaction is conveniently carried out at ambient temperature for a period of approximately fifteen minutes to approximately two hours. The organic liquid solution which contains the leuco compound is separated from the water layer. Additional alkali hydrosulfite is added to the organic liquid solution and the resulting mixture is azeotroped to remove the remaining traces of water. This dried solution of the leuco can then be interacted directly with an acylating agent in the manner described hereinabove. Alternatively, a metal reducing agent, for example, zinc dust may be used to reduce the benzo[a]phenoxazinium halide. This reaction is conveniently carried out in an excess of the alkanoic anhydride acylating agent thus resulting in no need for an inert reaction medium.

In accordance with the second of the aforementioned process aspects of this invention, the compounds of Formula III are obtained by reacting approximately one molecular proportion of a leuco compound of Formula VIII with about two molecular proportions of an acylating agent of Formula VI. When using an anhydride as the acylating agent, the reaction is conveniently carried out in an excess of the acylating agent which is utilized as both the reaction medium and as the reactant. Optionally, a small amount of an organic base, for example, pyridine may be used as a catalyst. The reaction is conveniently carried out at a temperature in the range of 90° C. to reflux of the mixture for periods of approximately thirty minutes to approximately four hours. The compounds of Formula III thus obtained are isolated by pouring the reaction mixture into ice water and extracting the desired products into a suitable water immiscible organic liquid, for example, toluene. The organic liquid layer containing the product is subsequently washed with water to remove inorganic salts and water-soluble organics and then treated with decolorizing charcoal, if desired. The resulting organic liquid solution of the product is then concentrated by conventional means such as evaporation or distillation. Alternatively, the compounds of Formula III can be obtained also by reacting approximately one molecular proportion of a leuco compound of Formula VIII with about two molecular proportions of an acyl halide (Formula VI; Z=halo). A solution of the leuco compound dissolved in an organic liquid is cooled to a temperature in the range of 60° to 80° C. and disodium phosphate and acyl halide, dissolved in the same organic liquid, is added. The reaction is conveniently carried out at the reflux temperature of the mixture for periods of approximately fifteen minutes to approximately nineteen hours. Water and additional disodium phosphate are added to the reaction mixture and the resulting mixture is heated at reflux temperature for a period of approximately thirty minutes to approximately one hour. The organic liquid solution containing the desired product is separated from the water layer, washed with water and concentrated by conventional means such as evaporation or distillation. The product of the concentration process is impure and further purification is desirable. The isolated product can be purified by conventional means such as recrystallization or reslurrying with a suitable organic liquid and then collected by filtration. Purification can also be effected by column chromatography. The material to be purified is dissolved in a suitable organic liquid and the solution is passed through a chromatography column which has been packed with a suitable substrate, for example, silica gel, cellulose or alumina. Numerous fractions are collected and analyzed to determine fraction(s) containing the desired product. The fraction(s) which contain the desired product are then combined (if more than one) and concentrated to obtain the product. The leuco compound of Formula VIII is conveniently prepared by reducing the corresponding benzo[a]phenoxazin-5-one of Formula VII with a reducing agent, for example, an alkali hydrosulfite. The reaction in which the leuco compound is prepared is conveniently carried out in a mixture of water and a suitable water immiscible organic liquid, for example, toluene or xylene in an inert atmosphere, for example, nitrogen. The reaction is carried out in the presence of an alkaline substance, for example, sodium carbonate or disodium phosphate using, as the reducing agent, an alkali hydrosulfite, for example, sodium hydrosulfite. The reaction is conveniently carried out at ambient temperature for a period of approximately fifteen minutes to approximately two hours. The organic liquid solution which contains the leuco compound is separated from the water layer. Additional alkali hydrosulfite is added to the organic liquid solution and the resulting mixture is azeotroped to remove the remaining traces of water. This dried solution of the leuco can then be interacted directly with an acylating agent in the manner described hereinabove. Alternatively, a metal reducing agent, for example, zinc dust may be used to reduce the benzo[a]phenoxazine-5-one. This reaction is conveniently carried out in an excess of the alkanoic acid anhydride acylating agent thus resulting in no need for an inert reaction medium.

The molecular structures of the compounds were assigned on the basis of the modes of synthesis and a study of their infrared, nuclear magnetic resonance and mass spectra.

The following examples will further illustrate the invention without, however, limiting it thereto.

EXAMPLE 1

A mixture of 14.0 g of 9-diethylamino-5-(N-benzylamino)benzophenoxazin-7-ium chloride, 75.0 ml of acetic anhydride, 5.0 ml of pyridine and 7.0 g of zinc dust was maintained at reflux temperature for approximately two hours. After cooling to room temperature, the reaction mixture was filtered to remove insolubles and the filter cake was washed twice, each time with 50.0 ml of acetone. The filtrate and the washes were combined and slowly poured into a mixture of water and toluene. After stirring the mixture for approximately thirty minutes, the organic extracts were separated, treated with decolorizing carbon, filtered, and the resulting clarified toluene solution was evaporated under reduced pressure to afford 15.17 g of 9-diethylamino-5-(N-acetyl-N-benzylamino)-12-acetylbenzo[a]phenoxazine (Formula II: $R=CH_3$; $R^1=C_6H_5CH_2$; $R^2=R^3=C_2H_5$), a pale brown powder which melted over the range of 86° to 91° C. A significant infrared maximum appeared 1670 cm$^{-1}$ (C=O;s). Significant maximum appeared in the mass spectrum at 493 (M$^+$) and was consistent with the assigned structure. The nuclear magnetic resonance spectrum was consistent with the assigned structure. A paper treated with an ink formulation of the product produced a strong blue-violet-colored image when traced with an applied voltage stylus.

EXAMPLE 2

The reaction vessel was purged of residual air with nitrogen and, while maintaining a nitrogen atmosphere, a mixture of 12.0 g of 9-dimethylamino-5-(N-benzylamino)benzophenoxazin-7-ium chloride, 500.0 ml of water, 500.0 ml of toluene, 12.0 g of sodium carbonate, and 15.0 g of sodium hydrosulfite was stirred for approximately fifteen minutes at room temperature. The layers were separated, the water layer was discarded and 200.0 ml of fresh toluene and 10.0 g of sodium hydrosulfite was added to the toluene solution. The resulting toluene mixture was azeotroped dry, cooled and 10.0 g of disodium phosphate and 15.0 ml of para-toluoyl chloride were added. The resulting reaction mixture was maintained at reflux of approximately three hours. After cooling to room temperature, 500.0 ml of water and 17.0 g of disodium phosphate was added to the reaction mixture and the resulting mixture was maintained at reflux for approximately ninety minutes. After cooling to room temperature, the layers were separated and the water layer was discarded. The organic solution was washed six times as follows: three washes with 800.0 ml water; one wash with 800.0 ml of saturated aqueous sodium carbonate solution; one wash with 800.0 ml water; and one wash with saturated aqueous sodium chloride solution. The toluene solution was treated with activated charcoal, filtered and evaporated under reduced pressure obtaining a dark gummy residue. This residue was dissolved in a 2:23 (V:V) mixture of ethyl acetate and toluene. The resulting solution was separated into various components by subjecting it to column chromatography using silica gel as the substrate. A total of forty-four fractions, each containing approximately twenty milliliters, were collected and each fraction was analyzed by thin layer chromatography. Fractions 1 to 14 and 32 to 44 were discarded. Fractions 15 to 27 were combined and concentrated by evaporation at reduced pressure to obtain 2.3 g of 5-[N-benzyl-N-(4-methylphenylcarbonyl)]amino-9-dimethylamino-12-(4-methylphenylcarbonyl) benzo[a]phenoxazine (Formula II: $R=4-CH_3C_6H_4$; $R^1=C_6H_5CH_2$; $R^2=R^3=CH_3$), a tancolored powder which melted at 202° to 204° C. A significant infrared maximum appeared at 1650 cm$^{-1}$ (C=O;m). A significant maximum appeared in the mass spectrum at 617 (M$^+$) and was consistent with the assigned structure. Fractions 28 to 31 were combined and concentrated to obtain 0.19 g of the product. Paper treated with an ink formulation of the product produced a violet-colored image when traced with an applied voltage stylus.

EXAMPLE 3

Proceeding in a manner similar to that described in Example 2 above, 12.0 g of 9-dimethylamino-5-benzylaminobenzo[a]phenoxazin-7-ium chloride was reacted in a mixture of 500.0 ml of water and 500.0 ml of toluene with 18.0 g of sodium hydrosulfite to obtain the corresponding leuco compound of the benzo[a]phenoxazine which in turn was reacted with 25.0 ml of orthochlorobenzoyl chloride to afford after recrystallization from a mixture of hexane and isopropanol, 1.77 g of 5-[N-benzyl-N-(2-chlorophenylcarbonyl)amino]-9-dimethylamino-12-(2-chlorophenylcarbonyl)benzo[a]phenoxazine (Formula II: $R=ClC_6H_4$; $R^1=C_6H_5CH_2$; $R^2=R^3=CH_3$), a tan-colored powder which melted at 229° to 232° C. A significant infrared maximum appeared at 1660 cm$^{-1}$ (C=O;m). Paper treated with an ink formulation of the product produces a violet-colored image when traced with an applied voltage stylus.

EXAMPLE 4

Following the procedure described in Example 2 above, 10.0 g of 9-diethylamino-5-benzylaminobenzo[a]phenoxazin-7-ium chloride was reacted in a mixture of 500.0 ml of water and 500.0 ml of toluene with 10.0 g of sodium hydrosulfite to obtain the leuco benzo[a]phenoxazine which was then reacted with 15.0 ml of benzoyl chloride to obtain after purification by column chromatography, 0.69 g of 9-N-benzyl-N-benzoylamino)-9-diethylamino-12-benzoylbenzo[a]phenoxazine (Formula II: $R=C_6H_5$; $R^1=C_6H_5CH_2$; $R^2=R^3=C_2H_5$), a tan powder which melted at 180° to 182° C. A significant infrared maximum appeared at 1655 cm$^{-1}$ (C=O;s). Paper treated with an ink formulation of the product produced a violet-colored image when traced with an applied voltage stylus.

EXAMPLE 5

In a manner similar to that described in Example 2 above, 10.0 g of 9-diethylamino-5-benzylaminobenzo[a]phenoxazin-7-ium chloride was reacted with 10.0 g of sodium hydrosulfite in a mixture of 500.0 ml of water and 500.0 ml of toluene to obtain the leuco benzo[a]phenoxazine compound which was further reacted with 13.5 ml of para-anisoyl chloride to obtain after purification utilizing column chromatography, 0.5 g of 5-[N-benzyl-N-(4-methoxyphenylcarbonyl)amino]-9-diethylamino-12-(4-methoxyphenylcarbonyl)benzo[a]phenoxazine (Formula II: $R=4-CH_3OC_6H_4$; $R^1=C_6H_5CH_2$; $R^2=R^3=C_2H_5$), a pink-colored gum. A significant infrared maximum appeared at 1650 cm$^{-1}$ (C=O;m). Paper treated with an ink formulation of the product produced a violet-colored image.

EXAMPLE 6

Proceeding in a manner similar to that described in Example 1 hereinabove, 12.0 g of 5-benzylamino-9- dimethylaminobenzo[a]phenoxazin-7-ium chloride was interacted with 60.0 ml of hexanoic anhydride and 5.0 g of zinc dust in the presence of 5.0 ml of pyridine to obtain after purification using column chromatography, 5-(N-benzyl-N-pentylcarbonylamino)-9-dimethylamino-12-pentylcarbonylbenzo[a]phenoxazine (Formula II: $R=CH_3(CH_2)_4$; $R^1=C_6H_5CH_2$; $R^2=R^3=CH_3$), a pale brown-colored gum. A significant infrared maximum appeared at 1670 cm$^{-1}$ ($C=O$;m). Paper treated with an ink formulation of the product produced a purple-colored image when traced with an applied voltage stylus.

It is contemplated that by following the procedure described in the foregoing examples, but employing the appropriate 5-(N-$R^1$-amino)-9-(N-$R^2$-N-$R^3$-amino)benzo[a]phenoxazinium halide of Formula IV with a reducing agent and the appropriate acylating agent of Formula VI, there will be obtained 5-(N-$R^1$-N-COR-amino)-9-(N-$R^2$-N-$R^3$-amino)-12-(R-CO)benzo[a]phenoxazine of Formula II, presented in Examples 7 to 25 in Table A hereinbelow.

and the acetone washes were combined and added slowly to approximately 400.0 ml of water. An oily liquid separated from the water and was extracted from the water with toluene. Subsequently, the toluene solution was washed with water and saturated sodium chloride solution, treated with activated carbon and clarified. The resulting toluene solution was evaporated to dryness. The residue obtained was dissolved in a mixture of ethyl acetate:toluene (2:23::V:V) and purified by passing the solution through a chromatography column packed with silica gel. Fractions 7 through 11 were combined, evaporated to dryness and the residue triturated with hexane to obtain 0.26 g of 5-methylcarbonyloxy-9-diethylamino-12-acetylbenzo[a]phenoxazine (Formula III: $R=CH_3$; $R^2=R^3=C_2H_5$), a pale brown-colored solid which melted at 64° to 72° C. Significant infrared maxima appeared at 1772 cm$^{-1}$ ($C=O$;m) and 1680 cm$^{-1}$ ($C=O$;s). Paper treated with an ink formulation of the product produced a strong purple-colored image when traced with an applied voltage stylus.

TABLE A

| Example No. | R | $R^1$ | $R^2$ | $R^3$ |
|---|---|---|---|---|
| 7 | $ClCH_2$ | $CH_3$ | $C_6H_5CH_2$ | $C_6H_5CH_2$ |
| 8 | $F_3C$ | $C_2H_5$ | $C_2H_5$ | $CH_3$ |
| 9 | $C_3H_5$ | $C_4H_9$ | $C_6H_5$ | $CH_3$ |
| 10 | $Cl_2CH$ | $CH_3$ | $C_4H_9$ | $C_4H_9$ |
| 11 | $C_5H_{11}$ | $C_3H_7$ | $4\text{-}CH_3C_6H_4CH_2$ | $4\text{-}CH_3C_6H_4CH_2$ |
| 12 | $BrCH_2$ | $CH_3$ | $4\text{-}NO_2C_6H_4CH_2$ | $CH_3$ |
| 13 | $2\text{-}BrC_2H_4$ | $C_6H_4CH_2$ | $CH_3$ | $C_6H_5$ |
| 14 | $2\text{-}BrC_2H_4$ | $CH_3$ | $3\text{-}ClC_6H_4CH_2$ | $C_2H_5$ |
| 15 | $3\text{-}ClC_3H_6$ | $C_4H_9$ | $C_4H_9$ | $C_4H_9$ |
| 16 | $2\text{-}(C_2H_5)C_3H_6$ | $CH_3$ | $C_2H_5$ | $3\text{-}BrC_6H_4CH_2$ |
| 17 | $5\text{-}BrC_5H_{11}$ | $C_2H_5$ | $2,4\text{-}Cl_2C_6H_3CH_2$ | $CH_3$ |
| 18 | $C_{11}H_{23}$ | $CH_3$ | $C_2H_5$ | $2,3\text{-}(CH_3)_2C_6H_3CH_2$ |
| 19 | $C_3H_5$ | $C_3H_7$ | $2,5\text{-}(CH_3)_2C_6H_3CH_2$ | $C_2H_5$ |
| 20 | $4\text{-}C_4H_9OC_6H_4$ | $CH_3$ | $2,6\text{-}Cl_2C_6H_3CH_2$ | $CH_3$ |
| 21 | $4\text{-}C_4H_9C_6H_4$ | $C_6H_5$ | $2\text{-}FC_6H_4CH_2$ | $C_4H_9$ |
| 22 | $2,4\text{-}Cl_2C_6H_3$ | $CH_3$ | $2\text{-}CH_3C_6H_4CH_2$ | $2\text{-}CH_3C_6H_4CH_2$ |
| 23 | $3,5\text{-}(CH_3O)_2C_6H_3$ | $4\text{-}CH_3C_6H_4CH_2$ | $4\text{-}CH_3C_6H_4CH_2$ | $C_2H_5$ |
| 24 | $3,5\text{-}(NO_2)_2C_6H_3$ | $4\text{-}ClC_6H_4CH_2$ | $C_2H_5$ | $C_2H_5$ |
| 25 | $2\text{-}IC_6H_4$ | $3\text{-}NO_2C_6H_4CH_2$ | $CH_3$ | $CH_3$ |

EXAMPLE 26

A mixture of 10.0 g of 9-diethylaminobenzo[a]phenoxazin-5-one, 75.0 ml of acetic anhydride and 10.0 g of zinc dust was maintained at approximately 80° C. for approximately thirty minutes. After the reaction mixture was cooled to room temperature, the solid present was collected by filtration and it was washed twice, each time with 25.0 ml of acetone. The filtrate It is contemplated that by following the procedure described in the foregoing example, but employing the appropriate 9-(N-$R^2$-N-$R^3$-amino)-benzo[a]phenoxazin-5-one of Formula VII with a reducing agent and the appropriate acylating agent of Formula VI, there will be obtained the corresponding 5-(RCOO)-9-(N-$R^2$-N-$R^3$-amino)-12-(RCO)-benzo[a]phenoxazine of Formula III, presented in Examples 27 to 45 in Table B hereinbelow.

TABLE B

| Example No. | R | $R^2$ | $R^3$ |
|---|---|---|---|
| 27 | $ClCH_2$ | $C_6H_5CH_2$ | $C_6H_5CH_2$ |
| 28 | $F_3C$ | $C_2H_5$ | $CH_3$ |
| 29 | $C_3H_5$ | $C_6H_5$ | $CH_3$ |
| 30 | $Cl_2CH$ | $C_4H_9$ | $C_4H_9$ |
| 31 | $C_5H_{11}$ | $4\text{-}CH_3C_6H_4CH_2$ | $4\text{-}CH_3C_6H_4CH_2$ |
| 32 | $BrCH_2$ | $4\text{-}NO_2C_6H_4CH_2$ | $CH_3$ |
| 33 | $2\text{-}BrC_2H_4$ | $CH_3$ | $C_6H_5$ |
| 34 | $2\text{-}BrC_2H_4$ | $3\text{-}ClC_6H_4CH_2$ | $C_2H_5$ |
| 35 | $3\text{-}ClC_3H_6$ | $C_4H_9$ | $C_4H_9$ |
| 36 | $2\text{-}(C_2H_5)C_3H_6$ | $C_2H_5$ | $3\text{-}BrC_6H_4CH_2$ |
| 37 | $5\text{-}BrC_5H_{11}$ | $2,4\text{-}Cl_2C_6H_3CH_2$ | $CH_3$ |
| 38 | $C_{11}H_{23}$ | $C_2H_5$ | $2,3\text{-}(CH_3)_2C_6H_3CH_2$ |
| 39 | $C_3H_5$ | $2,5\text{-}(CH_3)_2C_6H_3CH_2$ | $C_2H_5$ |
| 40 | $4\text{-}C_4H_9OC_6H_4$ | $2,6\text{-}Cl_2C_6H_3CH_2$ | $CH_3$ |
| 41 | $4\text{-}C_4H_9C_6H_4$ | $2\text{-}FC_6H_4CH_2$ | $C_4H_9$ |
| 42 | $2,4\text{-}Cl_2C_6H_3$ | $2\text{-}CH_3C_6H_4CH_2$ | $2\text{-}CH_3C_6H_4CH_2$ |
| 43 | $3,5\text{-}(CH_3O)_2C_6H_3$ | $4\text{-}CH_3C_6H_4CH_2$ | $C_2H_5$ |
| 44 | $3,5\text{-}(NO_2)_2C_6H_3$ | $C_2H_5$ | $C_2H_5$ |

TABLE B-continued

| Example No. | R | $R^2$ | $R^3$ |
| --- | --- | --- | --- |
| 45 | 2-$IC_6H_4$ | $CH_3$ | $CH_3$ |

What is claimed is:

1. A compound having the structural formula

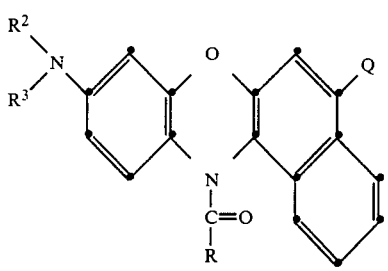

wherein:

Q represents [N-$R^1$-N-(RCO)amino] or (RCOO);

R represents non-tertiary $C_1$ to $C_{12}$ alkyl, $C_4$ to $C_8$ cycloalkyl, non-tertiary $C_1$ to $C_{12}$ alkyl substituted with halogen, phenyl or phenyl substituted by one to three of non-tertiary $C_1$ to $C_4$ alkyl, non-tertiary $C_1$ to $C_4$ alkoxy, nitro, halo, phenyl, cyano, or trihalomethyl; and $R^1$, $R^2$ and $R^3$ independently represent non-tertiary $C_1$ to $C_4$ alkyl, phenyl, phenyl substituted by one or two of halo, nitro, non-tertiary $C_1$ to $C_4$ alkyl or non-tertiary $C_1$ to $C_4$ alkoxy, benzyl or benzyl substituted in the benzene ring by one or two of halo, nitro, non-tertiary $C_1$ to $C_4$ alkyl or non-tertiary $C_1$ to $C_4$ alkoxy.

2. A compound according to claim 1 in which Q represents N-$R^1$-N-(RCO)amino having the structural formula

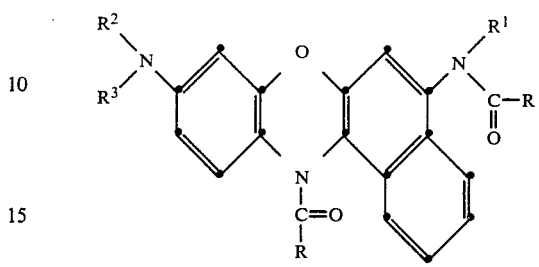

3. A 5-[N-(R-CO)-N-benzylamino]-9-(N-$R^2$-N-$R^3$-amino)-12-(R-CO)benzo[a]phenoxazine according to claim 2 wherein $R^1$ is benzyl.

4. 5-(N-Acetyl-N-benzylamino)-9-diethylamino-12-acetylbenzo[a]phenoxazine according to claim 2.

5. 5-[N-Benzyl-N-(4-methylphenylcarbonyl)amino]-9-dimethylamino-12-(4-methylphenylcarbonyl)benzo[a]phenoxazine according to claim 2.

6. A compound according to claim 1 in which Q represents RCOO having the structural formula

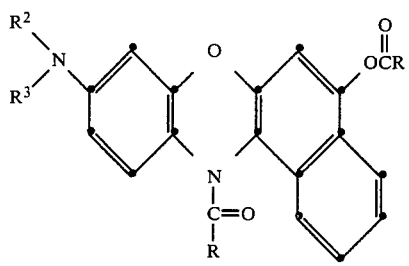

7. A 5-alkylcarbonyloxy-9-(N-$R^2$-N-$R^3$-amino)-12-alkylcarboxybenzo[a]phenoxazine according to claim 6 wherein R is non-tertiary $C_1$ to $C_{12}$.

8. 5-Methylcarbonyloxy-9-diethylamino-12-acetylbenzo[a]phenoxazine according to claim 7.

* * * * *